(12) United States Patent
Halverson

(10) Patent No.: US 9,388,448 B2
(45) Date of Patent: *Jul. 12, 2016

(54) SYSTEM AND METHOD FOR PROCESSING SAMPLES

(71) Applicant: 3M INNOVATIVE PROPERTIES COMPANY, St. Paul, MN (US)

(72) Inventor: Kurt J. Halverson, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 183 days.

This patent is subject to a terminal disclaimer.

(21) Appl. No.: 14/173,157

(22) Filed: Feb. 5, 2014

(65) Prior Publication Data

US 2014/0154731 A1 Jun. 5, 2014

Related U.S. Application Data

(63) Continuation of application No. 13/131,658, filed as application No. PCT/US2009/066218 on Dec. 1, 2009, now Pat. No. 8,647,508.

(60) Provisional application No. 61/139,158, filed on Dec. 19, 2008.

(51) Int. Cl.
*C12Q 1/02* (2006.01)
*G01N 1/40* (2006.01)
*G01N 35/00* (2006.01)

(52) U.S. Cl.
CPC ................. *C12Q 1/02* (2013.01); *G01N 1/4077* (2013.01); *G01N 35/00029* (2013.01); *G01N 2001/4088* (2013.01); *G01N 2035/00148* (2013.01); *Y10T 436/255* (2015.01); *Y10T 436/2575* (2015.01)

(58) Field of Classification Search
CPC . C12Q 1/02; G01N 1/4077; G01N 35/00029; G01N 2011/4088; Y10T 436/2575; Y10T 436/255
See application file for complete search history.

(56) References Cited

U.S. PATENT DOCUMENTS

| 4,539,256 A | 9/1985 | Shipman |
| 4,632,761 A | 12/1986 | Bowers |
| 4,698,311 A | 10/1987 | Hall |
| 4,726,989 A | 2/1988 | Mrozinski |
| 4,867,881 A | 9/1989 | Kinzer |
| 4,956,298 A | 9/1990 | Diekmann |
| 4,959,301 A | 9/1990 | Weaver |
| 5,120,594 A | 6/1992 | Mrozinski |
| 5,234,667 A | 8/1993 | Radtke |
| 5,260,360 A | 11/1993 | Mrozinski |
| 5,620,662 A | 4/1997 | Perlman |

(Continued)

*Primary Examiner* — David A Reifsnyder
(74) *Attorney, Agent, or Firm* — Qiang Han

(57) ABSTRACT

A system and method for processing samples. The system can include a loading chamber, a detection chamber positioned in fluid communication with the loading chamber, and a fluid path defined at least partially by the loading chamber and the detection chamber. The system can further include a filter positioned such that at least one of its inlet and its outlet is positioned in the fluid path. The method can include positioning a sample in the loading chamber, filtering the sample in the fluid path to form a concentrated sample and a filtrate, removing the filtrate from the fluid path at a location upstream of the detection chamber, moving at least a portion of the concentrated sample in the fluid path to the detection chamber, and analyzing at least a portion of the concentrated sample in the detection chamber for an analyte of interest.

23 Claims, 7 Drawing Sheets

(56) References Cited

U.S. PATENT DOCUMENTS

| | | | |
|---|---|---|---|
| 5,716,798 A | 2/1998 | Monthony |
| 5,770,440 A | 6/1998 | Berndt |
| 5,820,767 A | 10/1998 | Kane |
| 5,824,272 A | 10/1998 | Uchida |
| 5,833,860 A | 11/1998 | Kopaciewicz |
| 5,888,594 A | 3/1999 | David |
| 6,143,247 A | 11/2000 | Sheppard, Jr. |
| 6,197,579 B1 | 3/2001 | Van Vlasselaer |
| 6,221,655 B1 | 4/2001 | Fung |
| 6,386,699 B1 | 5/2002 | Ylitalo |
| 6,391,578 B2 | 5/2002 | Williams |
| 6,420,622 B1 | 7/2002 | Johnston |
| 6,458,553 B1 | 10/2002 | Colin |
| 6,566,508 B2 | 5/2003 | Bentsen |
| 6,617,002 B2 | 9/2003 | Wood |
| 6,627,159 B1 | 9/2003 | Bedingham |
| 6,696,286 B1 | 2/2004 | Halverson |
| 6,720,187 B2 | 4/2004 | Bedingham |
| 6,730,397 B2 | 5/2004 | Melancon |
| 6,734,401 B2 | 5/2004 | Bedingham |
| 6,814,935 B2 | 11/2004 | Harms |
| 6,867,342 B2 | 3/2005 | Johnston |
| 6,869,666 B2 | 3/2005 | Deeb |
| 6,987,253 B2 | 1/2006 | Bedingham |
| 7,026,168 B2 | 4/2006 | Bedingham |
| 7,164,107 B2 | 1/2007 | Bedingham |
| 7,223,364 B1 | 5/2007 | Johnston |
| 7,244,622 B2 | 7/2007 | Woudenberg |
| 7,435,933 B2 | 10/2008 | Bedingham |
| 7,445,752 B2 | 11/2008 | Harms |
| 8,647,508 B2 * | 2/2014 | Halverson ............ G01N 1/4077 210/257.2 |
| 2002/0128578 A1 | 9/2002 | Johnston |
| 2003/0036054 A1 | 2/2003 | Ladisch |
| 2003/0235677 A1 | 12/2003 | Hanschen |
| 2004/0038425 A1 | 2/2004 | Ferguson |
| 2004/0058408 A1 | 3/2004 | Thomas |
| 2004/0132208 A1 | 7/2004 | Burshteyn |
| 2004/0179974 A1 | 9/2004 | Bedingham |
| 2004/0259238 A1 | 12/2004 | Bashir |
| 2006/0188396 A1 | 8/2006 | Bedingham |
| 2006/0189000 A1 | 8/2006 | Bedingham |
| 2006/0228811 A1 | 10/2006 | Bedingham |
| 2006/0269451 A1 | 11/2006 | Bedingham |
| 2007/0003441 A1 | 1/2007 | Wohleb |
| 2007/0134784 A1 | 6/2007 | Halverson |
| 2007/0151924 A1 | 7/2007 | Mir |
| 2007/0196884 A1 | 8/2007 | Bodini |
| 2011/0039220 A1 | 2/2011 | Zhou |

* cited by examiner

SYSTEM AND METHOD FOR PROCESSING SAMPLES

RELATED APPLICATIONS

This is a continuation of U.S. patent application Ser. No. 13/131,658, filed May 27, 2011, now issued as U.S. Pat. No. 8,647,508, which is a national stage filing under 35 U.S.C. §371 of PCT/US2009/066218, filed Dec. 1, 2009, which claims the benefit of U.S. Provisional Patent Application No. 61/139,158, filed Dec. 19, 2008, the disclosures of which are incorporated herein by reference in their entirety.

FIELD

The present disclosure generally relates to a system and method for processing samples, and particularly, for processing liquid samples, and more particularly, for processing dilute liquid samples.

BACKGROUND

Testing aqueous samples for the presence of microorganisms (e.g., bacteria, viruses, fungi, spores, etc.) and/or other analytes of interest (e.g., toxins, allergens, hormones, etc.) can be important in a variety of applications, including food and water safety, infectious disease diagnostics, and environmental surveillance. For example, comestible samples, such as foods, beverages, and/or public water consumed by the general population may contain or acquire microorganisms or other analytes, which can flourish or grow as a function of the environment in which they are located. This growth may lead to the proliferation of pathogenic organisms, which may produce toxins or multiply to infective doses. By way of further example, a variety of analytical methods can be performed on samples of non-comestible samples (e.g., groundwater, urine, etc.) to determine if a sample contains a particular analyte. For example, groundwater can be tested for a microorganism or a chemical toxin; and urine can be tested for a variety of diagnostic indicators to enable a diagnosis (e.g., diabetes, pregnancy, etc.).

SUMMARY

One aspect of the present disclosure provides a method for processing samples. The method can include providing a loading chamber, providing a detection chamber positioned in fluid communication with the loading chamber, and providing a fluid path defined at least partially by the loading chamber and the detection chamber. The method can further include positioning a sample in the loading chamber, filtering the sample in the fluid path to form a concentrated sample and a filtrate, and removing the filtrate from the fluid path at a location upstream of the detection chamber. The method can further include moving at least a portion of the concentrated sample in the fluid path to the detection chamber, and analyzing the at least a portion of the concentrated sample in the detection chamber for an analyte of interest.

Another aspect of the present disclosure provides a system for processing samples. The system can include a loading chamber adapted to receive a sample, a detection chamber positioned in fluid communication with the loading chamber, and a fluid path defined at least partially by the loading chamber and the detection chamber. The system can further include a filter having an inlet and an outlet, the filter positioned such that at least one of the inlet and the outlet is positioned in the fluid path. The filter can be adapted to filter the sample to form a concentrated sample and a filtrate. The system can further include a filtrate outlet positioned such that the filtrate is removed from the fluid path at a location upstream of the detection chamber.

Other features and aspects of the present disclosure will become apparent by consideration of the detailed description and accompanying drawings.

DETAILED DESCRIPTION

Figure 1:
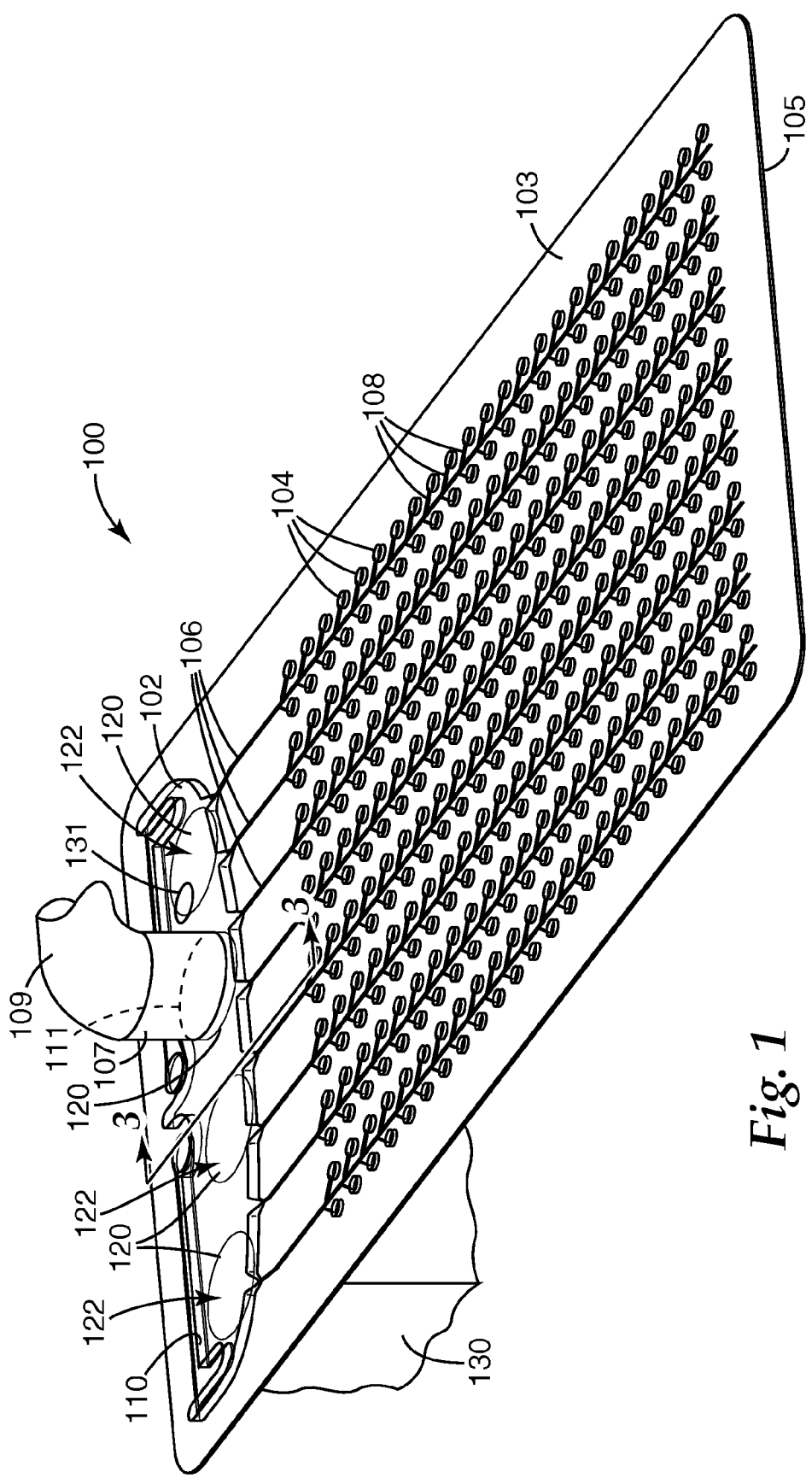
FIG. 1 is a front perspective view of a sample processing system according to one embodiment of the present disclosure, the sample processing system shown coupled to a vacuum source.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

In a variety of samples that are desired to be tested for one or more analytes of interest, the analyte(s) can be present in the sample at a low concentration and/or the sample volume can be large. Such situations can require that the sample be concentrated in order to reach an appropriate concentration of an analyte of interest so as to achieve a detection threshold of an analytical technique. In some existing systems and methods, membrane filtration can be employed to concentrate low-concentration samples, and can include capturing an analyte of interest onto microporous membranes for the purpose of identification and/or enumeration. Such methods can include vacuum filtration of a sample followed by sterile transfer of the membrane to another container (e.g., a Petri dish) containing the necessary nutrients that can then diffuse through the pores in the membrane during incubation to allow bacterial colonies to form on the membrane. The concentration of microorganisms in the original sample can then be determined by counting the number of colonies present on the membrane. Such methods can require numerous steps, including preparation of growth containers, sterilization and set-up of the filtration apparatus, and sterile transfer of the membrane from the device to the growth media. In addition, the procedure is limited to use on solid or semi-solid nutrient formulations to limit excess diffusion of bacteria of interest and/or water-soluble indicator species. Other existing systems and methods that include capturing cells on a support for further analysis or detection in one device do not allow for subsequent elution of the intact, captured cells or substantial removal of undesired filtrate from the device.

The present disclosure generally relates to a system and method for processing samples. In general, methods of the present disclosure can include concentrating samples to form a concentrated sample, moving at least a portion of the concentrated sample in a fluid path to a detection chamber (e.g., without exposing the concentrated sample to ambience), and analyzing the concentrated sample in the detection chamber to determine at least one of the presence, quantity, and/or viability of an analyte of interest. Systems of the present disclosure generally include means for concentrating and assaying a sample in one system without exposing the sample to ambience.

The present disclosure can provide sample concentration and assaying/detection in a single system, which can allow large sample volumes to be interrogated, can simplify the sample processing method, can reduce sample and environmental contamination, and can increase assay sensitivity and accuracy by removing undesired portions of the sample from the assay. The sample processing method can be simplified and the contamination can be reduced at least partially because by allowing sample concentration and detection to be contained within a single system of the present disclosure, a transfer step (e.g., of a collection membrane) into a second, separate device can be eliminated. In addition, in some embodiments of the present disclosure, where the sample is filtered in the system can be spatially separated from where it is assayed, which can improve assay sensitivity and accuracy, at least partially because undesired portions of the sample were removed from the assay.

The samples to be processed can be obtained in a variety of ways. For example, in some embodiments, the sample to be processed is itself a liquid sample, such as a dilute liquid sample and/or a dilute aqueous sample. In some embodiments, the sample can include the liquid resulting from washing or rinsing a source of interest (e.g., a surface, fomite, etc.) with a diluent. In some embodiments, the sample can include the filtrate resulting from filtering a liquid composition resulting from combining a source of interest with an appropriate diluent. That is, large insoluble matter, such as various foods, fomites, or the like, can be removed from a liquid composition in a first filtration step to form the sample that will be processed using a sample processing system and method of the present disclosure.

The term "source" can be used to refer to a food or nonfood desired to be tested for analytes. The source can be a solid, a liquid, a semi-solid, a gelatinous material, and combinations thereof. In some embodiments, the source can be provided by a substrate that was used, for example, to collect the source from a surface of interest. In some embodiments, the liquid composition can include the substrate, which can be further broken apart (e.g., during an agitation or dissolution process) to enhance retrieval of the source and any analyte of interest. The surface of interest can include at least a portion of a variety of surfaces, including, but not limited to, walls (including doors), floors, ceilings, drains, refrigeration systems, ducts (e.g., airducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof. All or a portion of the source can be used to obtain a sample that is to be processed using the sample processing system and method of the present disclosure.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

The term "nonfood" is generally used to refer to sources of interest that do not fall within the definition of "food" and are generally not considered to be comestible. Examples of nonfood sources can include, but are not limited to, clinical samples, cell lysates, whole blood or a portion thereof (e.g., serum), other bodily fluids or secretions (e.g., saliva, sweat, sebum, urine), feces, cells, tissues, organs, biopsies, plant materials, wood, soil, sediment, medicines, cosmetics, dietary supplements (e.g., ginseng capsules), pharmaceuticals, fomites, other suitable non-comestible materials, and combinations thereof.

The term "fomite" is generally used to refer to an inanimate object or substrate capable of carrying infectious organisms and/or transferring them. Fomites can include, but are not limited to, cloths, mop heads, towels, sponges, wipes, eating utensils, coins, paper money, cell phones, clothing (including shoes), doorknobs, feminine products, diapers, etc., portions thereof, and combinations thereof.

The term "analyte" is generally used to refer to a substance to be detected (e.g., by a laboratory or field test). A sample can be tested for the presence, quantity and/or viability of particular analytes. Such analytes can be present within a source (e.g., on the interior), or on the exterior (e.g., on the outer surface) of a source. Examples of analytes can include, but are not limited to, microorganisms, biomolecules, chemicals (e.g. pesticides, antibiotics), metal ions (e.g. mercury ions, heavy metal ions), metal-ion-containing complexes (e.g., complexes comprising metal ions and organic ligands), and combinations thereof.

A variety of testing methods can be used to identify, quantitate, and/or elucidate the viability of an analyte, including, but not limited to, microbiological assays, biochemical assays (e.g. immunoassay), or a combination thereof. Specific examples of testing methods that can be used include, but are not limited to, lateral flow assays, titration, thermal analysis, microscopy (e.g., light microscopy, fluorescent microscopy, immunofluorescent microscopy, scanning electron microscopy (SEM), transmission electron microscopy (TEM)), spectroscopy (e.g., mass spectroscopy, nuclear magnetic resonance (NMR) spectroscopy, Raman spectroscopy, infrared (IR) spectroscopy, x-ray spectroscopy, attenuated total reflectance spectroscopy, Fourier transform spectroscopy, gamma-ray spectroscopy, etc.), spectrophotometry (e.g., absorbance, fluorescence, luminescence, etc.), chromatography (e.g., gas chromatography, liquid chromatography, ion-exchange chromatography, affinity chromatography, etc.), electrochemical analysis, genetic techniques (e.g., polymerase chain reaction (PCR), transcription mediated amplification (TMA), hybridization protection assay (HPA), DNA or RNA molecular recognition assays, etc.), adenosine triphosphate (ATP) detection assays, immunological assays (e.g., enzyme-linked immunosorbent assay (ELISA)), cytotoxicity assays, viral plaque assays, techniques for evaluating cytopathic effect, culture techniques such as those that can be done using a growth medium (e.g., agar) and/or 3M™ PETRIFILM™ plates (e.g., and imaged, quantified and/or interpreted using a 3M™ PETRIFILM™ plate reader (3M Company, St. Paul, Minn.)), invasive cleavage reaction assays (e.g., INVADER® assay, available from Third Wave Technologies, Madison, Wis., a wholly-owned subsidiary of Hologic, Inc., Bedford, Mass.), SMARTDNA™ assay (available from Investigen, Inc., Hercules, Calif.), other suitable analyte testing methods, or a combination thereof.

The term "microorganism" is generally used to refer to any prokaryotic or eukaryotic microscopic organism, including without limitation, one or more of bacteria (e.g., motile or vegetative, Gram positive or Gram negative), viruses (e.g., Norovirus, Norwalk virus, Rotavirus, Adenovirus, DNA viruses, RNA viruses, enveloped, non-enveloped, human immunodeficiency virus (HIV), human Papillomavirus (HPV), etc.), bacterial spores or endospores, algae, fungi (e.g., yeast, filamentous fungi, fungal spores), prions, mycoplasmas, and protozoa. In some cases, the microorganisms of particular interest are those that are pathogenic, and the term "pathogen" is used to refer to any pathogenic microorganism. Examples of pathogens can include, but are not limited to, members of the family Enterobacteriaceae, or members of the family Micrococcaceae, or the genera *Staphylococcus* spp., *Streptococcus*, spp., *Pseudomonas* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., and *Corynebacterium* spp. Particular examples of pathogens can include, but are not limited to, *Escherichia* coli including enterohemorrhagic *E. coli* e.g., serotype 0157:H7, 0129:H11; *Pseudomonas aeruginosa; Bacillus cereus; Bacillus anthracis; Salmonella enteritidis; Salmonella enterica* serotype Typhimurium; *Listeria monocytogenes; Clostridium botulinum; Clostridium perfringens; Staphylococcus aureus*; methicillin-resistant *Staphylococcus aureus; Campylobacter jejuni; Yersinia enterocolitica; Vibrio vulnificus; Clostridium difficile*; vancomycin-resistant *Enterococcus;* and *Enterobacter [Cronobacter] sakazakii*. Environmental factors that may affect the growth of a microorganism can include the presence or absence of nutrients, pH, moisture content, oxidation-reduction potential, antimicrobial compounds, temperature, atmospheric gas composition and biological structures or barriers.

The term "biomolecule" is generally used to refer to a molecule, or a derivative thereof, that occurs in or is formed by an organism. For example, a biomolecule can include, but is not limited to, at least one of an amino acid, a nucleic acid, a polypeptide, a protein, a polynucleotide, a lipid, a phospholipid, a saccharide, a polysaccharide, and combinations thereof. Specific examples of biomolecules can include, but are not limited to, a metabolite (e.g., staphylococcal enterotoxin), an allergen (e.g., peanut allergen(s), egg allergen(s), pollens, dust mites, molds, danders, or proteins inherent therein, etc.), a hormone, a toxin (e.g., *Bacillus* diarrheal toxin, aflatoxin, *Clostridium difficile* toxin etc.), RNA (e.g., mRNA, total RNA, tRNA, etc.), DNA (e.g., plasmid DNA, plant DNA, etc.), a tagged protein, an antibody, an antigen, ATP, and combinations thereof.

The terms "soluble matter" and "insoluble matter" are generally used to refer to matter that is relatively soluble or insoluble in a given medium, under certain conditions. Specifically, under a given set of conditions, "soluble matter" is matter that goes into solution and can be dissolved in the solvent (e.g., diluent) of a system. "Insoluble matter" is matter that, under a given set of conditions, does not go into solution and is not dissolved in the solvent of a system. A source can include soluble matter and insoluble matter (e.g., cell debris). Insoluble matter is sometimes referred to as particulate(s) or debris and can include portions of the source material itself (i.e., from internal portions or external portions (e.g., the outer surface) of the source) or other source residue or debris resulting from an agitation process. The analyte of interest can be present in the soluble matter or the insoluble matter.

The term "diluent" is generally used to refer to a liquid added to a source material to disperse, dissolve, suspend, emulsify, wash and/or rinse the source. In addition, a diluent can be added to a system of the present disclosure during one or more of concentration, elution, and detection. In some embodiments, the diluent is a sterile liquid. In some embodiments, the diluent can include a variety of additives, including, but not limited to, surfactants, or other suitable additives that aid in dispersing, dissolving, suspending or emulsifying the source for subsequent analyte testing; rheological agents; antimicrobial neutralizers (e.g., that neutralize preservatives or other antimicrobial agents); enrichment or growth medium comprising nutrients (e.g., that promote selective growth of desired microorganism(s)) and/or growth inhibitors (e.g., that inhibit the growth of undesired microorganism(s)); pH buffering agents; enzymes; indicator molecules (e.g. pH or oxidation/reduction indicators); spore germinants; an agent to neutralize sanitizers (e.g., sodium thiosulfate neutralization of chlorine); an agent intended to promote bacterial resuscitation (e.g., sodium pyruvate); stabilizing agents (e.g., that stabilize the analyte(s) of interest, including solutes, such as sodium chloride, sucrose, etc.); or a combination thereof. In some embodiments, the diluent can include sterile water (e.g., sterile double-distilled water (ddH$_2$O)); one or more organic solvents to selectively dissolve, disperse, suspend, or emulsify the source; aqueous organic solvents, or a combination thereof. In some embodiments, the diluent is a sterile buffered solution (e.g., Butterfield's Buffer, available from Edge Biological, Memphis Tenn.). In some embodiments, the diluent is a selective or semi-selective nutrient formulation, such that the diluent may be used in the selective or semi-selective growth of the desired analyte(s) (e.g., bacteria). In such embodiments, the diluent can be incubated with a source for a period of time (e.g., at a specific temperature) to promote such growth and/or development of the desired analyte(s).

Examples of growth medium can include, but are not limited to, Tryptic Soy Broth (TSB), Buffered Peptone Water (BPW), Universal Pre-enrichment Broth (UPB), *Listeria* Enrichment Broth (LEB), Lactose Broth, Bolton broth, or other general, non-selective, or mildly selective media known to those of ordinary skill in the art. The growth medium can include nutrients that support the growth of more than one desired microorganism (i.e., analyte of interest).

Examples of growth inhibitors can include, but are not limited to, bile salts, sodium deoxycholate, sodium selenite, sodium thiosulfate, sodium nitrate, lithium chloride, potassium tellurite, sodium tetrathionate, sodium sulphacetamide, mandelic acid, selenite cysteine tetrathionate, sulphamethazine, brilliant green, malachite green oxalate, crystal violet, Tergitol 4, sulphadiazine, amikacin, aztreonam, naladixic acid, acriflavine, polymyxin B, novobiocin, alafosfalin, organic and mineral acids, bacteriophages, dichloran rose bengal, chloramphenicol, chlortetracycline, certain concentrations of sodium chloride, sucrose and other solutes, and combinations thereof.

The term "agitate" and derivatives thereof is generally used to describe the process of giving motion to a material or an object (e.g., a sample processing system of the present disclosure), for example, to break up, homogenize, mix, combine and/or blend various components/contents. For example, agitation can be used during one or more of sample concentration, elution, and detection. A variety of agitation methods can be used, including, but not limited to, manual shaking, mechanical shaking (e.g., linear shaking), sonic (e.g., ultrasonic) vibration, vortex stirring, mechanical stirring (e.g., by a magnetic stir bar, or another agitating aid, such as ball bearings), manual compression (e.g., manual beating, squeezing, kneading, pummeling, etc., and combinations thereof), mechanical compression (e.g., mechanical beating, squeezing, kneading, pummeling, etc., and combinations thereof), and combinations thereof.

The term "filtering" is generally used to refer to the process of separating matter by size, charge and/or function. For example, filtering can include separating soluble matter and a solvent (e.g., diluent) from insoluble matter, or filtering can include separating soluble matter, a solvent and relatively small insoluble matter from relatively large insoluble matter. As a result, filtering can refer to (1) any pre-filtering steps that are employed to obtain a sample that is to be processed using the sample processing systems and methods of the present disclosure, (2) any filtering step that is employed to concentrate the sample using the sample processing systems and methods of the present disclosure, or (3) both (1) and (2). A variety of filtration methods can be used, including, but not limited to, passing the liquid composition (e.g., comprising a source of interest, from which a sample to processed can be obtained) through a filter, other suitable filtration methods, and combinations thereof.

"Settling" is generally used to refer to the process of separating matter by density, for example, by allowing the more dense matter in the liquid composition (i.e., the matter having a higher density than the diluent and other matter in the mixture) to settle. Settling may occur by gravity or by centrifugation. The more dense matter can then be separated from the less dense matter (and diluent) by aspirating the less dense (i.e., unsettled or floating) and diluent from the more dense matter, decanting the less dense matter and diluent, or a combination thereof. Pre-settling steps can be used in addition to or in lieu of pre-filtering steps to obtain a sample that is to be processed using the sample processing systems and methods of the present disclosure.

A "filter" is generally used to describe a device used to separate the soluble matter (or soluble matter and relatively small insoluble matter) and solvent from the insoluble matter (or relatively large insoluble matter) in a liquid composition and/or to filter a sample during sample concentration. Examples of filters can include, but are not limited to, a woven or non-woven mesh (e.g., a wire mesh, a cloth mesh, a plastic mesh, etc.), a woven or non-woven polymeric web (e.g., comprising polymeric fibers laid down in a uniform or non-uniform process, which can be calendered), a surface filter, a depth filter, a membrane (e.g., a ceramic membrane (e.g., ceramic aluminum oxide membrane filters available under the trade designation ANOPORE from Whatman Inc., Florham Park, N.J.), a polycarbonate membrane (e.g., track-etched polycarbonate membrane filters available under the trade designation NUCLEOPORE from Whatman, Inc.)), a polyester membrane (e.g., comprising track-etched polyester, etc.), a sieve, glass wool, a frit, filter paper, foam, etc., and combinations thereof.

In some embodiments, the term "filtrate" is generally used to describe the liquid remaining after the insoluble matter (or at least the relatively large insoluble matter) has been separated or removed from a liquid composition. In some embodiments, the term "supernatant" is generally used to describe the liquid remaining after the more dense matter has been separated or removed from a liquid composition. Such a filtrate and/or supernatant can form a sample to be processed by the sample processing systems and methods of the present disclosure. Alternatively, the term "filtrate" can be used to describe the undesirable portions of a sample that are removed during sample concentration of the sample processing systems and methods of the present disclosure.

Sample concentration can include filtering a sample to obtain a concentrated sample, which can then be further processed and interrogated. As mentioned above, filtering can refer to separating matter by size, charge and/or function. While the embodiments described below and illustrated in FIGS. 1-6 can be used in a variety of sample processing methods of the present disclosure, the embodiments illustrated in FIGS. 1-5 are generally used to concentrate a sample of interest by size-filtration, and FIG. 6 is generally used to concentrate a sample of interest by charge- and/or function-filtration.

Figure 2:
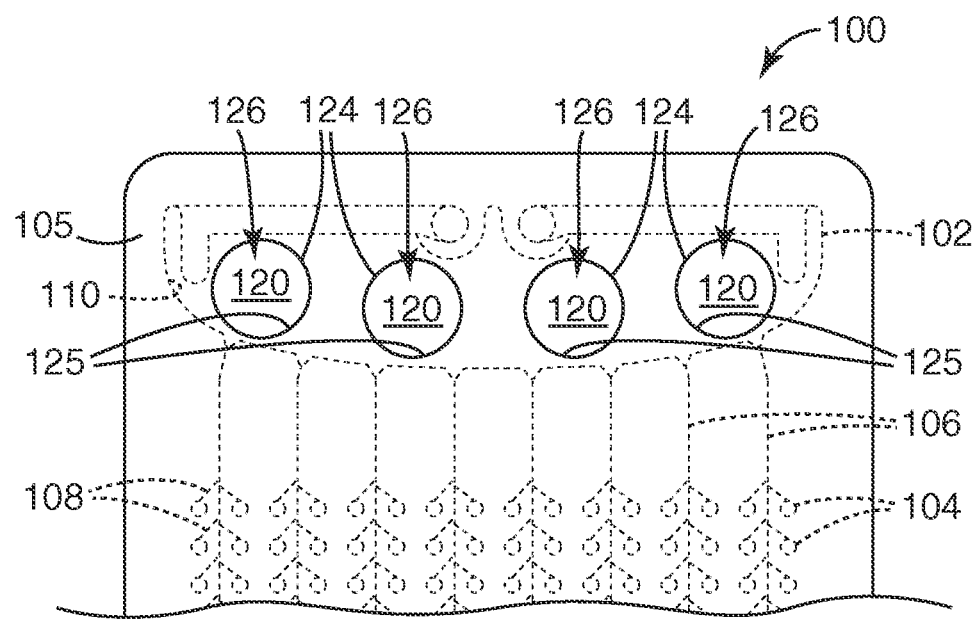
FIG. 2 a partial rear plan view of the sample processing system of FIG. 1.
Figure 3:
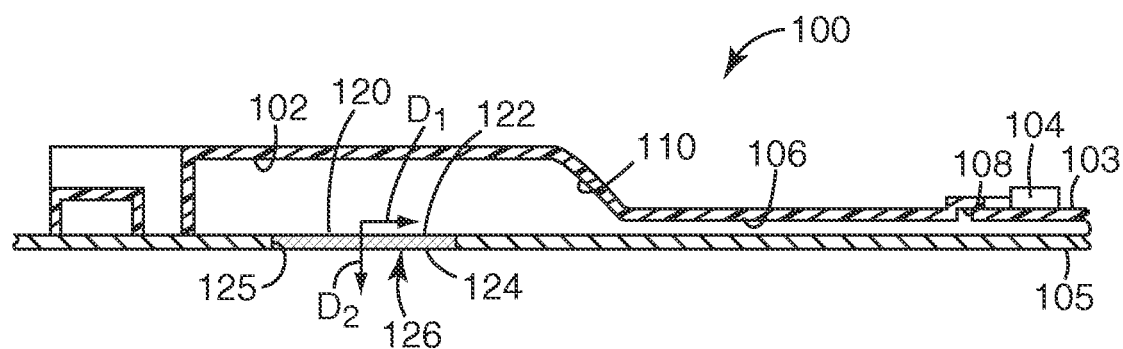
FIG. 3 is a partial side cross-sectional view the sample processing system of FIGS. 1 and 2, taken along line 3-3 in FIG. 1, with portions removed for clarity.

FIGS. 1-3 illustrate a sample processing system 100 according to one embodiment of the present disclosure. The sample processing system 100 includes a loading chamber 102, a plurality of detection chambers 104, and a plurality of primary channels 106 positioned to fluidly couple the plurality of detection chambers 104 to the loading chamber 102. The sample processing system 100 further includes a plurality of secondary channels 108, and each secondary channel 108 is positioned to fluidly couple one or more detection chambers 104 (i.e., one detection chamber 104 in the embodiment illustrated in FIGS. 1-3) to the primary channel 106.

The sample processing system 100 further includes a fluid path 110 that is at least partially defined by one or more of the loading chamber 102, the plurality of detection chambers 104, the plurality of primary channels 106, and the plurality of secondary channels 108. A sample can be analyzed in the detection chambers 104 to elucidate at least one of the presence, quantity and/or viability of the analyte(s) of interest.

The sample processing system 100 can further include or be coupled to a port 107 via which a sample can be introduced into the loading chamber 102. A valve can be positioned in fluid communication with the port 107 (e.g., in the port 107 itself) to control the movement of a sample into the loading chamber 102. In addition, the port 107 can be coupled to an upstream system or process via a connector 109. As mentioned above, the sample can be pre-filtered and/or pre-settled prior to being introduced into the sample processing system 100. Such a "pre-filter" can be positioned upstream of the connector 109, in the connector 109, in the port 107, and/or over an aperture 111 in the loading chamber 102 through which the sample passes as the sample is introduced into the loading chamber 102. In some embodiments, the port 107 includes a Luer lock to facilitate controlling introduction of a sample into the loading chamber 102 and/or connecting the port 107 to the connector 109 and/or any other upstream system.

Pre-filtering and/or pre-settling a liquid composition upstream of the sample processing system 100 to form a sample that will be introduced into the sample processing system 100 can be advantageous to enhance the purity of the material passing through the sample processing system 100 and enhance the capture of the analyte(s) of interest. In addition, pre-filtering and/or pre-settling can help avoid clogging the filters 120 or other downstream portions of the sample processing system 100. However, pre-filtering and/or pre-settling the sample or an upstream liquid composition is not necessary, and in some embodiments, the sample is introduced directly into the sample processing system 100 without being pre-filtered and/or pre-settled.

As shown in FIGS. 1-3, the sample processing system 100 can include a first major side 103 and a second major side 105. The first and second major sides 103 and 105 can be manufactured in a variety of ways using any suitable material or materials. Examples of suitable materials include polymeric materials (e.g., polypropylene, polyester, polycarbonate, polyethylene, etc.), metals (e.g., metal foils), etc., or combinations thereof. In some embodiments, one or more of the loading chamber 102, the detection chambers 104, the primary channels 106 and the secondary channels 108 can be formed in one side 103/105 of the sample processing system 100, while the opposite side 105/103 is provided in a generally flat sheet-like configuration. For example, in some embodiments, one or more of the loading chamber 102, the detection chambers 104, the primary channels 106, and the secondary channels 108 can be formed in the first major side 103 in a polymeric sheet, for example, that has been molded, vacuum-formed, thermoformed, or otherwise processed. The second major side 105 can then be provided as, for example, a sheet of metal foil, polymeric material (e.g., a polymeric film), multi-layer composite, etc., or a combination thereof, that can be coupled to the first major side 103. In some embodiments, the materials can be selected for the first and second major sides 103 and 105 that exhibit good water barrier properties.

As shown in FIGS. 1-3, the sample processing system 100 can further include one or more filters 120 positioned in the loading chamber 102. Each filter 120 can include an inlet 122 and an outlet 124, and each filter 120 can be positioned such that at least one of the inlet 122 and the outlet 124 is positioned in the fluid path 110. For example, in the embodiment illustrated in FIGS. 1-3, the filter inlet 122 is positioned in the fluid path 110, and the outlet 124 is positioned such that any filtrate formed by the filter 120 is removed from the fluid path 110 via the filter outlet 124. As a result, the filter 120 defines a filter fluid path 125 (see FIGS. 2 and 3). As such, the fluid path 110 can be referred to as a "primary fluid path" of the system 100, and the filter fluid path 125 can be referred to as a "secondary fluid path," and in some embodiments, the secondary fluid path 125 can be oriented at an angle with respect to the primary fluid path 110. For example, as shown in FIG. 3, the fluid path 110 is configured such that fluid can flow in the fluid path 110 generally along a first direction $D_1$, and the filter 120 is arranged such that fluid can flow through the filter 120 in the filter fluid path 125 generally along a second direction $D_2$, and by way of example only, the first direction $D_1$ and the second direction $D_2$ are shown as being oriented substantially perpendicularly with respect to one another, although other angles of orientation are possible. In some embodiments, as shown in FIG. 6, the filter fluid path 125 can be oriented in line with the fluid path 110 of the sample processing system 100, which is described in greater detail below.

Each filter 120 can be adapted to form a concentrated sample and a filtrate. The sample processing system 100 can include an outlet 126, i.e., a filtrate outlet, for removing the filtrate of the sample, or the undesired portions of the sample, from the fluid path 110, and particularly, for removing the filtrate from the fluid path 110 at a location upstream of the detection chambers 104. In some embodiments, as shown in FIGS. 1-3 (and FIGS. 4-5, described below), the filter 120 is positioned such that the filter outlet 124 is directed out of the fluid path 110, and, as a result, the filtrate outlet 126 includes the filter outlet 124. That is, in the embodiment in FIGS. 1-3, the filter 120 is positioned such that portions of a sample flowing through the filter 120 (i.e., the filtrate) will be directed out of the fluid path 110, and particularly, away from the detection chambers 104.

In some embodiments, the filtrate outlet 126 can be in fluid communication with the fluid path 110 and positioned adjacent a downstream side of the filter 120 (but does not necessarily include the filter outlet 124), such that the filtrate is removed from the fluid path 110 upstream of the detection chambers 104. In some embodiments, the filtrate outlet 126 can be positioned in fluid communication with the fluid path 110 at a location downstream of the filter 120 and upstream of the detection chambers 104 (e.g., as shown in the embodiment illustrated in FIG. 6 and described below). Whether the filtrate outlet 126 includes the filter outlet 124, is adjacent the filter outlet 124, and/or is in fluid communication with the fluid path 110 at a location downstream of the filter 120, the filtrate outlet 126 can be positioned such that the filtrate can be removed from the fluid path 110 of the sample processing system 100 at a location upstream of the detection chambers 104.

A sample can be filtered using the filters 120 by employing a pressure differential across each filter 120. That is, a pressure differential can be established between the upstream side (i.e., the inlet 122) and the downstream side (i.e., the outlet 124) of each filter 120. In some embodiments, the pressure differential can be established by applying positive pressure (e.g., using an upstream manual pump, such as a syringe, bulb, or the like, a mechanical pump, or a combination thereof) to the upstream side of the filter 120 and/or by applying negative pressure to the downstream side of the filter 120. Furthermore, in some embodiments, a portion of the sample processing system 100 can be deformable to create the pressure differential. For example, in some embodiments, the loading chamber 102 can be deformable to force the sample through the filters 120. In embodiments in which positive pressure is applied to an upstream side of the filter(s) 120, one or more obstructions or seals can be moved into a position that obstructs and/or seals a downstream portion of the fluid path 110 to inhibit the unconcentrated sample from prematurely moving into the detection chambers 104. Such obstructions and/or seals can be reversible, such that the fluid path 110 can be reopened when necessary.

In some embodiments, a vacuum source 130 can be coupled to the sample processing system 100, such that the vacuum source 130 is in fluid communication with the fluid path 110 via the filtrate outlet 126. In embodiments in which the filtrate outlet 126 includes or is in line with the filter outlet 124, the vacuum source 130 can be coupled to the filter outlet 124 to remove the filtrate of the sample of interest from the fluid path 110. The vacuum source 130 can include, but is not limited to, a mechanical pump, a manual pump such as a syringe-plunger combination, etc., or a combination thereof that creates a reduced pressure. In embodiments employing negative pressure on the downstream side of the filters 120, the entire fluid path 110 can be evacuated as well, such that obstructions and/or seals do not need to be employed to inhibit the unconcentrated sample from prematurely moving into the detection chambers 104.

When positive pressure is applied to the upstream side of the filter 120 and/or negative pressure is applied to the downstream side of the filter 120, a sample can be moved through the filter 120 to form a concentrated sample that is retained by the filter 120 (e.g., according to size, charge, and/or function) and a filtrate that passes through the filter 120 and out of the sample processing system 100, and optionally, to waste or another receptacle. The sample processing system 100 can further include an aperture 131 (see FIG. 1) to which a port and/or valve can be coupled. The aperture 131 can function as a vent when a sample is introduced into the loading chamber 102 and/or when the sample is filtered using the filters 120. Alternatively, or in addition, at least a portion of the loading chamber 102 can deform and/or collapse as the sample is filtered, for example, in response to negative pressure.

In some embodiments, the same process can be used to introduce a sample into the sample processing system 100 and to filter the sample. For example, in some embodiments, positive and/or negative pressure can be applied across the loading chamber 102, for example, across the upstream side of the aperture 111 and the downstream side of the filters 120, such that a sample is moved into the loading chamber 102 via the aperture 111, concentrated on the filters 120, and a filtrate of the sample is removed from the fluid path 110 of the sample processing system 100 via the filter outlets 124 (i.e., also functioning as the filtrate outlets 126). As such, the sample can be introduced into the sample processing system 100 and concentrated in the sample processing system 100 in one simultaneous step, or in a plurality of sequential steps.

In some embodiments, the sample is filtered to completion (i.e., substantially all liquid can be removed from the sample), and in some embodiments, the sample can be partially filtered, such that some liquid remains in the concentrated sample after filtration.

After the sample has been filtered using the filters 120 to form a concentrated sample on each filter 120, one or more washing solutions can optionally be introduced into the loading chamber 102 to wash the concentrated sample on each filter 120. The introduction of the one or more washing solutions can follow the same process as the initial sample introduction and/or filtering process.

Furthermore, an elution solution can be added to the loading chamber 102, for example, following the same process as the initial sample introduction process. However, in general (and unlike washing solutions), the elution solution will not be passed through the filters 120. That is, the filter outlets 124 can be covered to close the filters 120 to ambience when an elution solution is added to the loading chamber 102. Alternatively, in some embodiments, the filters 120 can be removed and plugged or sealed with a similarly-sized object. The elution solution can include the same diluent that the sample comprised or a different material. The elution solution can be selected to elute all or a portion of the concentrated sample (i.e., one or more analytes of interest) from the filters 120 and/or to inhibit the elution of others portions of the concentrated sample (i.e., one or more non-target analytes that may be present in the sample). In some embodiments, the volume of elution solution added to the sample processing system 100 can be controlled such that all of the volume is moved into the detection chambers 104 following elution.

Optionally, the sample processing system 100 can be agitated to facilitate the elution of all or a portion of the concentrated sample from the filters 120. In addition, in some embodiments, the sample processing system 100 can be incubated to promote the growth of one or more microorganisms of interest.

After all or a portion of the concentrated sample has been eluted from one or more of the filters 120, all or a portion of the concentrated sample can be moved in the fluid path 110 (i.e., without exposing the concentrated sample to ambience) to the detection chambers 104. That is, the concentrated sample (or a portion thereof) can be moved into one or more of the plurality of primary channels 106, into one or more of the secondary channels 108, and into one or more of the detection chambers 104.

In some embodiments, the phrase "without exposing to ambience" and derivations thereof refers to not removing the sample and/or concentrated sample from the sample processing system 100 during the transfer between the loading chamber 102 and the detection chambers 104 (e.g., to prevent spills or contamination, to facilitate sample handling, to minimize sample loss, etc.), such that the sample/concentrated sample remains in the fluid path 110 of the sample processing system 100 from sample introduction, concentration, elution, and transfer to the detection chambers 104. However, not being exposed to ambience does not necessarily mean that the sample processing system 100 is closed to gas-exchange or that other liquids cannot be introduced into the sample processing system 100. For example, in some embodiments, the loading chamber 102, one or more detection chambers 104, one or more primary channels 106, one or more secondary channels 108, a portion thereof, or a combination thereof, is gas-permeable, or includes a gas-permeable film or membrane (e.g., to allow aerobic bacteria to continue to have access to oxygen). For example, in some embodiments, at least one wall defining at least one of the detection chamber 104, the secondary channel 108, the primary channel 106, and the loading chamber 102 can be porous and can be adapted to allow gas exchange (e.g., without being liquid-permeable).

The concentrated sample can be moved into detection chambers 104 in a variety of ways, including, but not limited to, employing a pressure differential, centrifuging, employing capillary action (e.g., wicking), controlling the surface energy of any surface in the fluid path 110 between the filter 120 and the detection chamber 104, etc., or a combination thereof.

Employing a pressure differential can include applying positive pressure to fill the detection chambers 104 and/or vacuum filling the detection chambers 104. For example, any of the above described means for applying positive pressure can be employed, including, but not limited to, using an upstream manual and/or mechanical pump, employing a deformable loading chamber 102 (e.g., bulb-like), or combinations thereof. Vacuum filling of the detection chambers 104 can be accomplished, for example, if the detection chambers 104 are gas-permeable and liquid-impermeable, such that a vacuum source can be applied to the second major side 105 of the sample processing system 100 adjacent the back side of the detection chambers 104 to move the concentrated sample from the filters 120 to the detection chambers 104. Such gas-permeability can also be employed to vent the detection chambers 104 to facilitate filling under positive pressure.

Centrifuging can be employed particularly in embodiments in which the analyte(s) of interest represent the more dense matter in the concentrated sample, such that the concentrated sample can be separated by density. Centrifuging can include placing the sample processing system 100 in a centrifuge to facilitate moving the concentrated sample in the desired direction. For example, the sample processing system 100 can be oriented such that the most dense matter will be directed into the detection chambers 104 during centrifugation.

In the centrifugation step, the centrifugation g-force and/or duration necessary to move the concentrated sample into the detection chambers 104 can depending on one or more of the composition of the concentrate sample, the analyte(s) of interest, the shape, dimensions and surface energy of the filters 120, the surface energy of the concentrated sample, and the like. In some embodiments, the centrifugation can be performed according to the processes described in Bedingham, et al., U.S. Pat. No. 6,627,159, entitled "Centrifugal filling of sample processing devices," which is incorporated herein by reference. In some embodiments, it may be desired to fill substantially all of the detection chambers 104 of the sample processing system 100 with the concentrated sample (e.g., in enumeration assays).

In some embodiments, it may be desired to concentrate substantially all of the concentrated sample in one or more terminal detection chambers 104 (e.g., in presence/absence assays). In such embodiments, the g-force and/or duration necessary to move all of the concentrated sample to a terminal position of the sample processing system 100 can depend on the size and density of the analyte, the density and viscosity of the diluent (e.g., the elution solution used), the volume of concentrated sample, and/or the distance the concentrated sample will be required to travel to reach the detection chambers 104 (e.g., the length of the primary channels 106 and secondary channels 108). The sedimentation velocity (V, in centimeters per second (cm/s)) can be approximated using the formula:

$$V=2ga^2(\rho1-\rho2)/9\eta$$

where g=acceleration in cm/s$^2$ (i.e., g-force in gs*980 cm/s$^2$), $\rho1$=analyte density in g/cm$^3$, $\rho2$=density of media (e.g., diluent, elution solution, etc.) in g/cm$^3$, $\eta$=coefficient of viscosity in poises (g/cm/s), and a=analyte radius in centimeters (assuming a spherical shape). In some centrifuges (e.g., some laboratory centrifuges), the g-force can be determined by the rotational speed (e.g., in revolutions per minute (RPM)) and the distance of the sample from the center of the rotor (i.e. the sample experiences a higher g-force at the same rotational speed if it is placed further away from the rotor). The sedimentation velocity can be calculated using the above equation, and then the centrifugation time (i.e., duration) can be calculated by dividing the distance the concentrated sample needs to travel by the sedimentation velocity. Alternatively, the desired time and distance can be used to estimate a sedimentation velocity, and the necessary g-force can then be calculated using the above equation.

In some embodiments, the g-force in the centrifugation step can be at least about 50 g (e.g., 50*9.8 m/s$^2$ on earth, at sea level), in some embodiments, at least about 500 g, and in some embodiments, at least about 5000 g. In some embodiments, the g-force in the centrifugation step can be no greater than about 20,000 g, in some embodiments, no greater than about 10,000 g, and in some embodiments, no greater than about 7500 g.

In some embodiments, the duration of the centrifugation step can be at least about 10 seconds, in some embodiments, at least about 1 minutes, and in some embodiments, at least about 2 minutes. In some embodiments, the duration of the centrifugation step can be no greater than about 60 minutes, in some embodiments, no greater than about 30 minutes, and in some embodiments, no greater than about 10 minutes.

As mentioned above, in some embodiments, capillary action (e.g., wicking) can be used to move the concentrated sample into the detection chambers 104. For example, one or more of the primary channels 106 and the secondary channels 108 can be adapted to facilitate moving the concentrated sample by capillary action from the loading chamber 102 into the detection chambers 104. In some embodiments, one or more of the primary channels 106 and the secondary channels 108 can include a plurality of microchannels to further facilitate wicking the concentrated sample into the detection chambers 104.

Furthermore, in some embodiments, the surface energy of any of the surfaces defining the fluid path 110 can be controlled to facilitate moving the concentrated sample from the filters 120 to the detection chambers 104. For example, in some embodiments, one or more surfaces of one or more of the primary channels 106 can be modified (e.g., with a hydrophilic coating or surface treatment) to facilitate movement of the concentrated sample (e.g., an aqueous concentrated sample) along the respective primary channels 106 into the detection chambers 104. In addition, or alternatively, in some embodiments, one or more surfaces defining the fluid path 110 can be modified to facilitate movement of the concentrated sample off of the respective surface and toward another area. For example, in some embodiments, the loading chamber 102 can be surface modified (e.g., with a hydrophobic coating or surface treatment) to facilitate movement of the concentrated sample (e.g., an aqueous concentrated sample) away from the surfaces of the loading chamber 102 and toward other areas, such as the primary channels 106.

After the concentrated sample has been moved into the detection chambers 104, the concentrated sample can be inhibited from moving out of the detection chambers 104, which can be accomplished in a variety of ways, including, but not limited to, obstructing or sealing at least a portion of the fluid path 110 upstream of the detection chambers 104, employing aspect ratios that minimize diffusion of the concentrated sample out of the detection chambers 104, etc., or a combination thereof.

In some embodiments, one or more of the primary channels 106 and the secondary channels 108 can be obstructed and/or sealed to inhibit the concentrated sample from moving out of the detection chambers 104 and/or back upstream of the detection chambers 104 using one or more of adhesives, melt bonding, folding, crimping, etc., and combinations thereof. For example, the sealing methods and systems described in Bedingham, et al., PCT Publication No. WO 02/01180, which is incorporated herein by reference, can be employed in the present disclosure. Such sealing methods can be employed, for example, in embodiments such as the sample processing system 100 illustrated in FIGS. 1-3, in which the primary channels 106 are substantially parallel to one another along their length, and in which the secondary channels 108 are relatively short, such that sealing at least the most downstream portions of the primary channels 106 (e.g., simultaneously, as facilitated by their parallel arrangement) can effectively inhibit movement of the concentrated sample out of the detection chambers 104.

In some embodiments, the concentrated sample can be inhibited from moving out of the detection chambers 104 by exploiting capillary forces in the sample processing system 100 and/or by exploiting the surface tension of the concentrated sample. That is, the concentrated sample can be inhibited from moving out of a particular detection chamber 104 by ensuring that any portion of the fluid path 110 (e.g., the secondary channel 108 (or the primary channel 106 in embodiments in which a secondary channel 108 is not employed)) that is fluidly connected to the detection chamber 104 has an aspect ratio relative to the detection chamber 104 that minimizes diffusion (fluid movement) from the detection chamber 104 into an upstream portion of the fluid path 110. That is, the relationship between the cross-sectional area of the fluid path 110 ($A_p$) (e.g., at the outlet of the secondary channel 108) and the volume (V) of the detection chamber 104 from which fluid may move into the fluid path 110 can be controlled to inhibit diffusion from the detection chamber 104 into an upstream portion of the fluid path 110. In addition, or alternatively, the aspect ratio between a primary channel 106 and a particular secondary channel 108 can be controlled to inhibit movement of the concentrated sample upstream into a primary channel 106.

For example, in some embodiments, the ratio of the cross-sectional area of the fluid path 110 ($A_p$) (e.g., at the outlet of the secondary channel 108) to the volume (V) of the detection chamber 104 from which fluid may move into the fluid path 110, i.e., $A_p$:V, can range from about 1:25 to about 1:500, in some embodiments, can range from about 1:50 to about 1:300, and in some embodiments, can range from about 1:100 to about 1:200. Said another way, in some embodiments, the fraction of $A_p$/V can be at least about 0.01, in some embodiments, at least about 0.02, and in some embodiments, at least about 0.04. In some embodiments, the fraction of $A_p$/V can be no greater than about 0.005, in some embodiments, no greater than about 0.003, and in some embodiments, no greater than about 0.002. Reported in yet another way, in some embodiments, the fraction of V/$A_p$, or the ratio of V to $A_p$, can be at least about 25 (i.e., 25 to 1), in some embodiments, at least about 50 (i.e., about 50 to 1), and in some embodiments, at least about 100 (i.e., about 100 to 1). In some embodiments, the fraction of V/$A_p$, or the ratio of V to $A_p$), can be no greater than about 500 (i.e., about 500 to 1), in some embodiments, no greater than about 300 (i.e., about 300 to 1), and in some embodiments, no greater than about 200 (i.e., about 200 to 1).

In use, a liquid composition can be pre-filtered and/or pre-settled to form a liquid sample. Alternatively, a liquid sample can be used itself without requiring any pre-filtering or pre-settling process. The sample can be introduced into the loading chamber 102, for example, via the aperture 111 in the loading chamber 102. The sample can then be filtered with the filters 120 to form a concentrated sample on the filters 120, while the filtrate is removed from the fluid path 110 of the sample processing system 100, and is sent to waste or another receptacle. After the concentrated sample has been formed on the filters 120 (e.g., by size-restriction), one or more wash solutions can optionally be introduced into the sample processing system 100 following the same process as used for sample introduction and removed from the sample processing system 100 following the sample concentration process. Following any washing steps employed, an elution solution can be introduced into the sample processing system 100. The elution solution can be adapted to elute the concentrated sample from the filters 120, and can be adapted to selectively elute the portions of interest of the concentrated sample from the filters 120. The sample processing system 100 can be agitated to facilitate eluting the concentrated sample from the filters 120, such that a liquid is formed in the loading chamber 102 comprising the elution solution and at least a portion of the concentrated sample. The concentrated sample (and any elution solution) can then be moved into the detection chamber 104 using any of the methods described above. After the concentrated sample has been moved into the detection chambers 104, the concentrated sample can be inhibited from moving out of the detection chambers 104, or upstream of the detection chambers 104 by any of the methods described above.

When the portions of interest of the concentrated sample have been moved into (and retained) in the detection chambers 104, the sample processing system 100 can be used to enrich the analyte(s) of interest, if present, in the concentrated sample. That is, the detection chambers 104 can include one or more reagents, such as enrichment media. The reagents can be provided in the detection chambers 104 in liquid or solid (e.g., dry powder) form, can be adsorbed or coated onto an inner surface of the detection chambers 104, or a combination thereof. Enrichment media can include any media necessary to grow (e.g., in cell population) any analyte(s) of interest and/or to suppress the growth of any non-target analytes, and can include any of the materials listed above with respect to the diluent. Furthermore, the detection chambers 104 can include any of a variety of indicators, such as color-change indicators, fluorescent indicators, chemiluminescent indicators, etc., and combinations thereof, in order to facilitate elucidating at least one of the presence, quantity and/or viability of the analyte(s) of interest.

In addition, or alternatively, in some embodiments, the sample can be enriched in the loading chamber 102 (e.g., in the presence of enrichment media and at appropriate enrichment conditions, such as time, temperature, pressure, humidity, etc.), for example, to permit one or more doubling cycles of bacteria of interest. After sufficient enrichment has occurred, the enriched sample can be concentrated (e.g., using the filter(s) 120), and the concentrated sample can be eluted into the detection chambers 104. In addition, or alternatively, enrichment media can be added to the loading chamber 102 after the sample has been concentrated, and the concentrated sample can be enriched (and optionally, refiltered) in the loading chamber 102 prior to being moved into the detection chambers 104.

Thus, a sample can be introduced, concentrated and/or analyzed using the sample processing system 100, without ever 're-opening' the sample processing system 100 after the sample is first introduced into the sample processing system 100. As a result, the sample processing system 100 can be a fully integrated sample processing device, in which a sample can be analyzed or interrogated while minimizing both contamination and sample loss.

The sample processing system 100 illustrated in FIGS. 1-3 is shown by way of example only, however, it should be understood that a variety of alternative shapes, numbers and configurations of the components of the sample processing system 100 can be employed without departing from the spirit and scope of the present disclosure. In addition, a variety of configurations, features and/or processes described in Bedingham et al. 'Sample Processing' patents and publications can be employed in the present disclosure, namely, U.S. Pat. Nos. 6,627,159, 6,720,187, 6,734,401, 6,814,935, 6,869,666, 6,987,253, 7,026,168, 7,164,107, 7,435,933, 7,445,752; US Patent Application Publication Nos. 2004/179974, 2006/188396, 2006/189000, 2006/228811, 2006/269451; and PCT Patent Application Publication Nos. WO 02/00347, 02/01180, 02/01181, 02/086454, 02/090091, and 2004/058405, all of which are incorporated herein by reference.

For example, the loading chamber 102 is shaped to facilitate moving the concentrated sample into the primary channels 106 (e.g., by centrifugation), but it should be understood that any desired shape or configuration can be employed.

Furthermore, the primary channels 106 are illustrated as being substantially parallel, which can facilitate moving the concentrated sample into the detection chambers and can also facilitate sealing the primary channels simultaneously, but other shapes and arrangements of the primary channels 106 are possible.

Moreover, in embodiment shown in FIGS. 1-3, the primary channels 106, the secondary channels 108 and the detection chambers 104 are arranged in arrays, such that each array includes forty-eight detection chambers 104, forty-eight secondary channels 108, and one primary channel 106; there are eight arrays fluidly coupled to the loading chamber 102; and there are four filters 120 employed in the loading chamber 102. However, a variety of numbers and arrangements of detection chambers 104, secondary channels 108, primary channels 106, filters 120 and loading chambers 102 can be employed. For example, a variety of numbers and arrangements of detection chambers 104, secondary channels 108 and primary channels 106 can be employed in each array, and as few arrays as one or as many as structurally possible can be employed in the sample processing system 100. In addition, multiple loading chambers 102 can be employed, such that there is one array fluidly coupled to each loading chamber 102 (such as the embodiment illustrated in FIGS. 4-5, described below). For example, in some embodiments, the sample processing system 100 can include one loading chamber 102, one filter 120, one primary channel 106, and one detection chamber 104.

In addition, some embodiments do not include any secondary channels 108, and in some embodiments, each secondary channel 108 can be an aperture between the detection chamber 104 and a respective primary channel 106, providing fluid communication between the detection chamber and the primary channel 106.

Furthermore, in the embodiment illustrated in FIGS. 1-3, the sample processing system 100 is shown as including one large loading chamber 102 with multiple filters 120. However, in some embodiments, the one large loading chamber 102 can instead include one large filter 120 (e.g., sized and/or shaped corresponding to the loading chamber 102). In some embodiments, the sample processing system 100 can include as few or as many filters 120 as structurally possible.

Moreover, in the embodiment illustrated in FIGS. 1-3, the secondary channels 108 are shown in pairs, exiting off of the respective primary channel 106 at the same downstream location. However, a variety of other configurations of secondary channels 108 can be employed, such as off-set locations, etc., as further described in the above-mentioned Bedingham et al. patents and patent publications.

In addition, the sample processing system 100 can be formed in a variety of ways, such as the processes described in the above-mentioned Bedingham et al. patents and publications.

Figure 4:
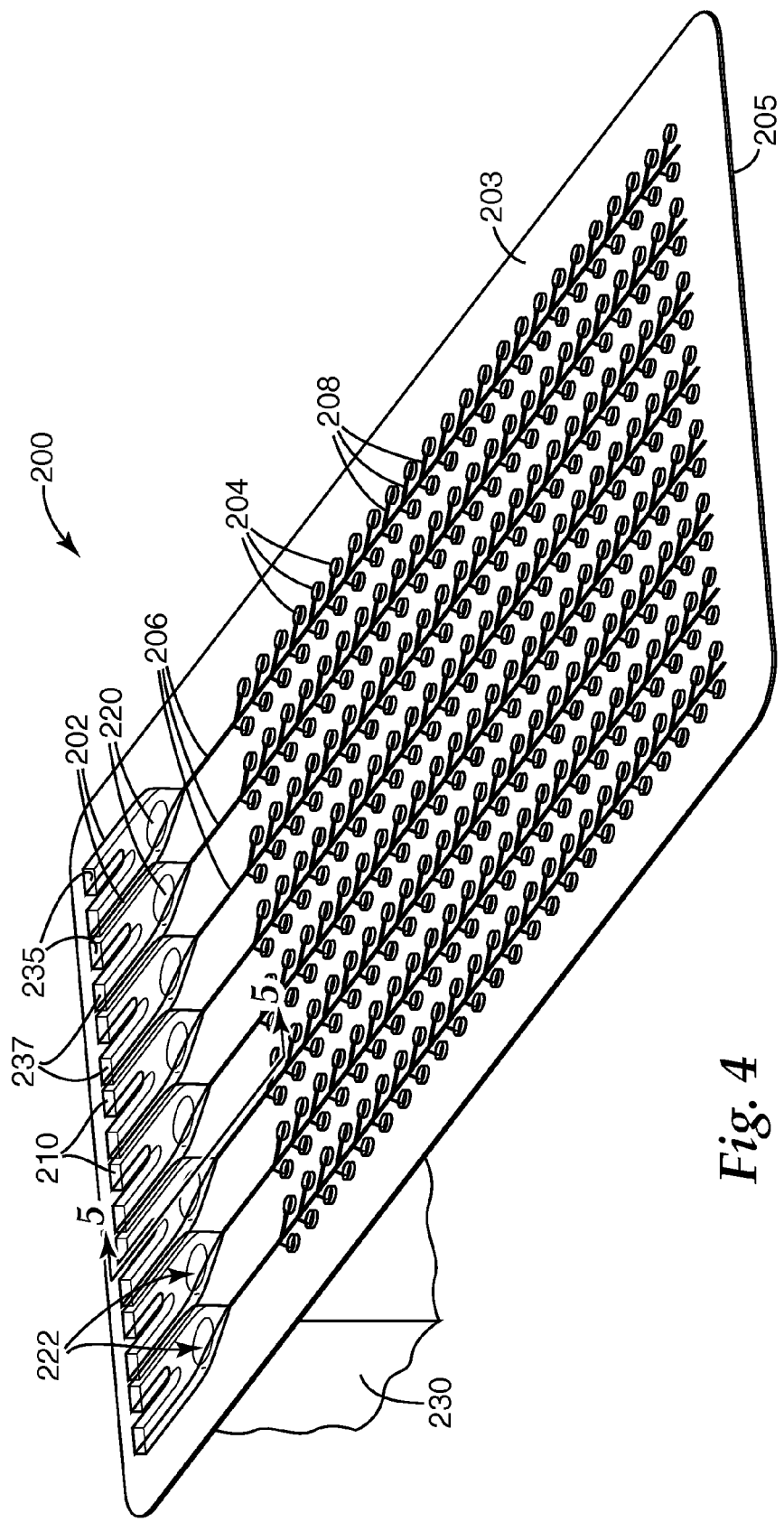
FIG. 4 is a front perspective view of a sample processing system according to another embodiment of the present disclosure.
Figure 5:
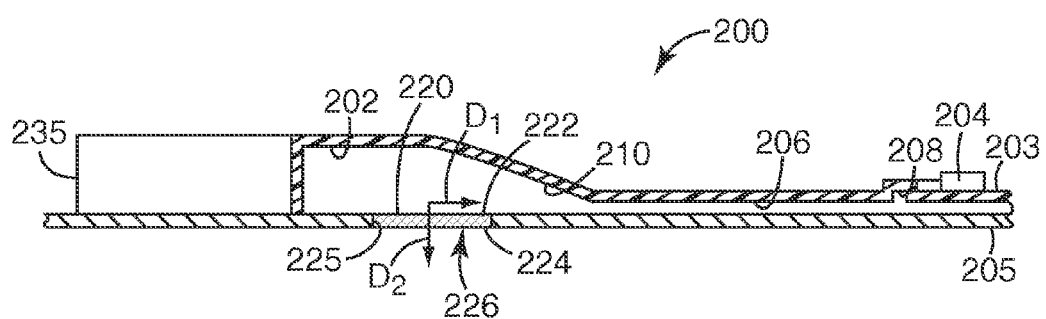
FIG. 5 is a partial side cross-sectional view of the sample processing system of FIG. 4, taken along line 5-5 in FIG. 4.
Figure 6:
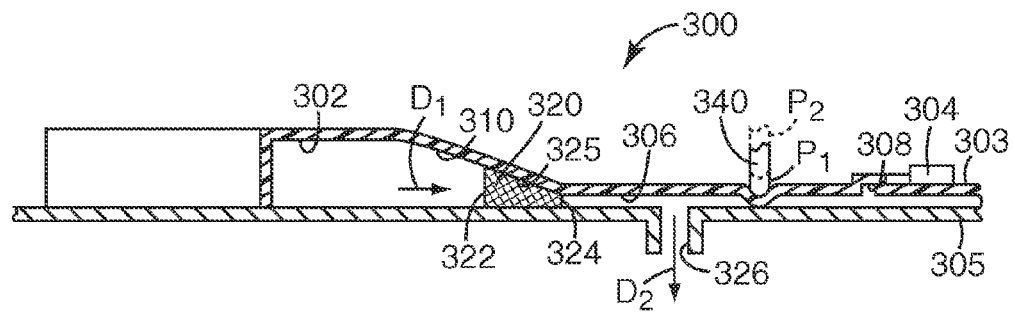
FIG. 6 is a partial side cross-sectional view of a sample processing system according to another embodiment of the present disclosure.

FIGS. 4-5 illustrate a sample processing system 200 according to another embodiment of the present disclosure. The sample processing system 200 shares many of the same elements and features described above with reference to the illustrated embodiment of FIGS. 1-3. Accordingly, elements and features corresponding to elements and features in the illustrated embodiments of FIGS. 1-3 are provided with the same reference numerals in the 200 series. Reference is made to the description above accompanying FIGS. 1-3 for a more complete description of the features and elements (and alternatives to such features and elements) of the embodiment illustrated in FIGS. 4-5.

The sample processing system 200 includes a first major side 203, a second major side 205, and a plurality of sample processing arrays 201 (eight are shown in FIG. 4 by way of example only). By way of example only, each sample processing array 201 is illustrated in FIG. 4 as including one loading chamber 202, a plurality of detection chambers 204 (forty-eight are shown in FIG. 4 by way of example only), one primary channel 206, and a plurality of secondary channels 208 (forty-eight, i.e., one per detection chamber 104, are shown in FIG. 4 by way of example only) positioned to fluidly couple the plurality of detection chambers 204 to the primary channel 206.

Each sample processing array 201 can define a fluid path 210, such that the sample processing system 200 includes a plurality of fluid paths 210 that, in some embodiments, can be fluidly isolated from one another. Each fluid path 210 is at least partially defined by the respective array's loading chamber 202, plurality of detection chambers 204, primary channel 206, and plurality of secondary channels 208.

The same sample, or a plurality of samples, can be concentrated and analyzed using the sample processing system 200. For example, in some embodiments, the sample processing system 200 can be used to simultaneously process a variety of samples in parallel. Samples can be introduced into the sample processing system 200 using apertures similar to the aperture 111 and any ports or valves coupled thereto, as illustrated in FIG. 1 and described above. Additionally, or alternatively, in some embodiments, samples can be introduced into the loading chambers 202 by puncturing a wall defining the loading chamber 202 (e.g., with a needle and syringe). In addition, if necessary, introduction of the sample can be facilitated by venting the loading chamber 202 as the sample is introduced. For example, an aperture similar to the aperture 131 illustrated in FIG. 1 as described above can be employed. Additionally, or alternatively, in some embodiments, a wall defining the loading chamber 202 can be punctured to vent the loading chamber 202. For example, as described in the Bedingham et al. patents and publications, a first aperture can be created (e.g., in a rear wall 235) in one portion of the loading chamber 202, and a second aperture can be created in another location (e.g., in the other rear wall 237 of the generally U-shaped loading chamber 202) to introduce the sample into the loading chamber 202. The U-shaped loading chambers 202 are shown in FIGS. 4-5 by way of example only, however, it should be understood that a variety of shapes and configurations can be employed for the loading chambers 202.

As shown in FIGS. 4-5, each sample processing array 201 can further include one or more filters 220 positioned in the loading chamber 202. Each filter 220 can include an inlet 222 and an outlet 224, and each filter 220 can be positioned such that at least one of the inlet 222 and the outlet 224 is positioned in the fluid path 210. Similar to the embodiment illustrated in FIGS. 1-3, the filter inlet 222 of each filter 220 illustrated in FIGS. 4-5 is positioned in the fluid path 210, and the outlet 224 of each filter 220 is positioned such that any filtrate formed by the filter 220 is removed from the fluid path 210 via the filter outlet 224. As a result, each filter 220 defines a filter fluid path 225 (see FIG. 5). As such, the fluid path 210 can be referred to as a "primary fluid path" of the system 200, or the respective array 201, and the filter fluid path 225 can be referred to as a "secondary fluid path," and in some embodiments, the secondary fluid path 225 can be oriented at an angle with respect to the primary fluid path 210. For example, as shown in FIG. 5, the fluid path 210 is configured such that fluid can flow in the fluid path 210 generally along a first direction $D_1$, and the filter 220 is arranged such that fluid can flow through the filter 220 in the filter fluid path 225 generally along a second direction $D_2$, and by way of example only, the first direction $D_1$ and the second direction $D_2$ are shown as being oriented substantially perpendicularly with respect to one another, although other angles of orientation are possible.

Each filter 220 can be adapted to form a concentrated sample and a filtrate. Each sample processing array 201 can include an outlet 226, i.e., a filtrate outlet, for removing the filtrate of the sample, or the undesired portions of the sample, from the fluid path 210, and particularly, for removing the filtrate from the fluid path 210 at a location upstream of the detection chambers 204. In some embodiments, as shown in FIGS. 4-5, each filter 220 is positioned such that the filter outlet 224 is directed out of the fluid path 210, and, as a result, the filtrate outlet 226 includes the filter outlet 224. That is, in the embodiment in FIGS. 4-5, each filter 220 is positioned such that portions of a sample flowing through the filter 220 (i.e., the filtrate) will be directed out of the fluid path 210, and particularly, away from the detection chambers 204.

In use, the sample processing system 200, and each sample processing array 201 can be used to process a sample similarly to the methods, and alternatives thereto, described above with respect to the sample processing system 100 illustrated in FIGS. 1-3.

FIG. 6 illustrates a sample processing system 300 according to another embodiment of the present disclosure. The sample processing system 300 shares many of the same elements and features described above with reference to the illustrated embodiments of FIGS. 1-5. Accordingly, elements and features corresponding to elements and features in the illustrated embodiments of FIGS. 1-5 are provided with the same reference numerals in the 300 series. Reference is made to the description above accompanying FIGS. 1-5 for a more complete description of the features and elements (and alternatives to such features and elements) of the embodiment illustrated in FIG. 6.

The sample processing system 300 includes a first major side 303 and a second major side 305. The sample processing system 300 further includes one or more loading chamber 302, one or more detection chambers 304, one or more primary channels 306, and one or more secondary channels 308. The sample processing system 300 further includes a fluid path 310 that is at least partially defined by the one or more loading chambers 302, the one or more detection chambers 304, the one or more primary channels 306, and the one or more secondary channels 308 (if employed). For simplicity, the sample processing system 300 will be described, with reference to FIG. 6, as including one loading chamber 302, one detection chamber 304, one primary channel 306, and one secondary channel 308, but it should be understood that the various arrangements and configurations described above with respect to the sample processing system 100 illustrated in FIGS. 1-3 can also be employed in the sample processing system 300 illustrated in FIG. 6

As shown in FIG. 6, the sample processing system 300 can further include one or more filters 320 positioned in the loading chamber 302. The filter 320 can include an inlet 322 and an outlet 324, and the filter 320 is shown as being positioned such that both the inlet 322 and the outlet 324 are positioned in the fluid path 310. As a result, the filter 320 defines a filter fluid path 325. As such, the fluid path 310 can be referred to as a "primary fluid path" of the system 300, and the filter fluid path 325 can be referred to as a "secondary fluid path" In the embodiment illustrated in FIG. 6, the secondary fluid path 325 is in line with the primary fluid path 310, such that fluid can flow in the fluid path 310 generally along a first direction $D_1$, and the filter 320 is arranged such that fluid can also flow through the filter 320 generally along the first direction $D_1$.

In some embodiments employing a filter fluid path 325 that is generally in line with the fluid path 210, the filter 320 can be configured, for example, to filter the sample by charge- and/or function-filtration. As such, the filter 320 can be configured to retain (e.g., temporarily) the portions of the sample of interest (e.g., the portions including the analyte(s) of interest), while the remainder of the sample (i.e., the filtrate) passes through the filter 320.

In such embodiments, the sample processing system 300 can include a filtrate outlet 326 positioned downstream of the filter 320 but upstream of the detection chamber 304 such that any fluid moved through the filter 320 can be removed from the fluid path 310 before being moved into the detection chambers 304. For example, the filtrate outlet 326 can allow fluid to flow out of the fluid path 310 and generally along a second direction $D_2$, which can be oriented at an angle with respect to the first direction $D_1$. By way of example only, the first direction $D_1$ and the second direction $D_2$ can be oriented substantially perpendicularly with respect to one another, although other angles of orientation are possible.

In some embodiments, as shown in FIG. 6, at least a portion of the fluid path 310 (e.g., a portion of the fluid path 310 that is positioned downstream of the filter 320 and upstream of the detection chamber 304) can be adapted to change between a first, closed state in which the filter 320 and the detection chambers are not in fluid communication and a second, open state in which the filter 320 and the detection chamber 304 are in fluid communication. As a result, the fluid path 310 can be in the first, closed state during filtration and removal of the filtrate (i.e., during formation of the concentrated sample), and the fluid path 310 can be in the second, open state during movement of the concentrated sample to the detection chamber 304.

Accordingly, in some embodiments, the sample processing system can include a member (obstruction, seal, etc.) 340 positioned to obstruct the fluid path 310 at a position that is located downstream of the filtrate outlet 324 and upstream of the detection chamber 304. In some embodiments, the member 340 can be movable between a first position $P_1$ in which the member is obstructing the fluid path 310 (e.g., in which the member 340 is causing the fluid path 310 to be in its first, closed state) and a second position $P_2$ in which the member 340 is not obstructing the fluid path 310 (e.g., in which the member 340 is causing the fluid path 310 to be in its second, open state).

As a result, the member 340 can be positioned in the first position $P_1$ during filtration and removal of the filtrate via the filtrate outlet 326 (i.e., during formation of the concentrated sample), and the member 340 can be positioned in the second position $P_2$ during movement of the concentrated sample to the detection chamber 304.

In some embodiments, additionally, or alternatively, selectively actuatable valves can be positioned in the fluid path 310 to control fluid movement between the filter 320 and the detection chamber 304.

Such constructions of the fluid path 310 (e.g., employing one or more of movable member(s) 340, valves, etc.) can be useful, for example, in embodiments in which positive pressure is used to move the sample through the filter 320. In embodiments employing negative pressure, for example, such constructions may not be necessary, as the entire fluid path 310 can be evacuated during filtration of the sample.

The filtrate outlet 326 can be also adapted to change between a first, open state in which the downstream side of the filter 320 (i.e., the outlet 324) is in fluid communication with ambience (or another downstream system or process) via the filtrate outlet 326, and a second, closed state in which the downstream side of the filter 320 (i.e., the outlet 324) is not in fluid communication with ambience or another device, via the filtrate outlet 326. Constructions such as those described above (e.g., movable member(s), valves, etc.) can be used to control fluid movement through the filtrate outlet 326, when necessary.

In use, the sample processing system 300 can be used to process a sample similarly to the methods, and alternatives thereto, described above with respect to the sample processing system 100 illustrated in FIGS. 1-3.

After the sample has been concentrated on the filter 320, the filter 320 and concentrated sample can be washed with one or more washing solutions (and one or more steps) following the same process described above, wherein the washing solution can be removed from the fluid path 310 via the filtrate outlet 326. Following the optional washing step(s), an elution solution can be added to the loading chamber 302 following the same procedure as was used to introduce a sample to the sample processing system 300. Such an elution solution can be adapted to disrupt any interaction between the filter 320 and the analyte(s) of interest (or the portions of interest in the concentrated sample), the filtrate outlet 326 can be changed to its second, closed state, the member 340 can be moved into its second position $P_2$, and the concentrated sample (or the portions of interest) can be moved in the fluid path 310 to the detection chamber 304.

While the sample processing systems 100, 200 and 300 are illustrated and described separately above, it should be understood that any combination of the above-described sample processing systems 100, 200, and 300 and methods are possible and within the spirit and scope of the present disclosure.

As described above, a variety of filters 120, 220, 320 can be employed in the sample processing system 100, 200, 300 of the present disclosure to concentrate a sample by size, charge and/or function. For example, filters 120, 220, 320 can be employed that carry a surface charge for the ionic capture of soluble analytes. By way of example only, such a surface charge may be useful in embodiment in which bacteria undergo a lysis step, for example, prior to concentration and/or movement into the detection chambers 104. For example, in some embodiments, nucleic acid can be captured on a filter 120, 220, 320 comprising glass fiber, followed by washing and elution into the detection chambers 104.

Furthermore, the sample processing systems 100, 200, 300 can be useful in assaying a variety of analyte(s) of interest. For example, any of the sample processing systems 100, 200, 300 disclosed herein can be used in infectious disease diagnostics where a low number of bacteria may be present in the original sample. Bacterial concentration can be achieved using one or more filters 120, 220, 320, followed by cell lysis, optional DNA purification, and finally elution into the detection chambers 104 that can contain reagents for identifying the bacteria (e.g., polymerase chain reaction primers and probes, etc.).

The following working examples are intended to be illustrative of the present disclosure and not limiting.

EXAMPLES

Example 1

Bacterial Enumeration Assay

Sample Processing System

Four sample processing systems 100 were assembled according to the embodiment illustrated in FIGS. 1-3, the four systems serving as four replicates in this example. The sample processing systems 100 each included a single loading chamber 102, 8 primary channels 106, and 384 secondary channels 108 and detection chambers 104, each primary channel 106 providing fluid communication between the loading chamber 102 and 48 secondary channels 108 and detection chambers 104. A first Luer port was coupled to the aperture 111, and a second Luer port was coupled to the aperture 131 of each sample processing system. Each sample processing system 100 further included four filters 120 positioned in the loading chamber 102, and each filter 120 was 10 mm in diameter and punched from a METRICEL® membrane disc filter (0.45-micrometer pore size, available from Pall Corporation, East Hills, N.Y.).

The first major side 103 was formed of polypropylene, and the loading chamber 102, primary channels 106, secondary channels 108 and detection chambers 104 were form by thermoforming. The second major side 105 was formed of an aluminum foil coated with a silicone-polyurea adhesive, as generally described in Bedingham, et al., U.S. Pat. No. 7,026,168.

The sample processing systems 100 were assembled according to the methods described in Bedingham et al., PCT Application Publication No. WO 02/01180, with additional processing steps for the addition of the filters 120, apertures 111, 131 and corresponding Luer ports, etc.

To form each sample processing system replicate, the assemblies were placed in a machined tool designed to mate with the embossed pattern in the first major side 103 while fully contacting the flat land area between embossed features. The assemblies and tools were then placed in a laminating press (Model 810, available from Sencorp, Inc., Hyannis, Mass.) at 200° F. for 5 seconds at 60 psi to bond the first major side 103 to the second major side 105.

Filtration Process

A vacuum manifold designed to mate to the second major side 105 of each sample processing system replicate under the loading chamber 102 was assembled and coupled to a vacuum flask, which was, in turn, coupled to a vacuum source. To ensure sealing between the manifold and the device, a rubber gasket was cut to size and placed between the manifold and the sample processing system 100. To support the rear side of the filters 120 during filtration, a layer of a semi-rigid nonwovern material (CELESTRA® spunbonded polypropylene, available from Fiberweb Inc., London, England) was placed between the gasket and the manifold. A piece of silicone tubing approximately 8" in length having a ⅛-inch internal diameter was cut and coupled to one of the Luer ports using a barbed adapter to serve as the connector 109.

Sterile $H_2O$ was introduced into each sample processing system via the connector 109 using a 3-cc syringe to fill the loading chamber 102 and to wet the filters 120. The syringe was removed and the connector 109 was then placed into 100 mL of an approximately 1 cfu/mL sample of E. coli (ATCC MG1655) prepared in Butterfield's Buffer from an overnight culture of approximately $10^9$ organisms/mL grown in BBL™ Trypticase Soy Broth (available from Becton, Dickinson and Co., Franklin Lakes, N.J.). The sample was filtered through the filters 120, capturing the bacteria and allowing the buffer solution to flow out of the fluid path 110 of the respective sample processing system 100 and into the vacuum flask.

Elution and Movement into Detection Chambers

A stock solution of 4-methylumbelliferyl phosphate (MU-phos) in Luria Broth (LB) having a concentration of 250 µg/mL was prepared by adding 15.5 g of LB to 1000 mL of sterile water in a Pyrex bottle. The bottle was partially sealed and autoclaved to sterilize the solution. Once sufficiently cooled, 250 mg of MU-phos was added to the LB to make the stock solution. The solution was swirled vigorously to ensure dissolution of the indicator.

After filtering the sample using the sample processing systems 100 to concentrate the sample, the stopper from one Luer port was opened to create a vent. 1 mL of the above-described stock solution of MU-phos in LB was introduced to the loading chamber 102 through the second Luer port using a 1-cc syringe. The backside of the filters 120 were covered using autoclave tape (3M™ ESPE™ autoclave steam indicator, available from 3M Company, St. Paul, Minn.). Both ports were then sealed using Luer caps. To release captured bacteria from the filters 120, the device was placed on a vortex mixer with a flat platform (a VWR® Mini Vortexer, speed setting 6, available from VWR International, West Chester, Pa.) for 30 seconds. The sample processing system replicates were then centrifuged according to the process outlined in Bedingham, et al., U.S. Pat. No. 6,627,159 (i.e., at 2000 RPM for 2 min.) to move the eluted concentrated sample into the detection chambers 104 via the primary channels 106. The primary channels 106 were then sealed using a stylus device, as described in Bedingham, et al., PCT Application Publication No. WO 02/01180. Each sample processing system replicate was then incubated for 18 hours at 37° C.

Fluorescene Imaging of Detection Chambers

Figure 7:
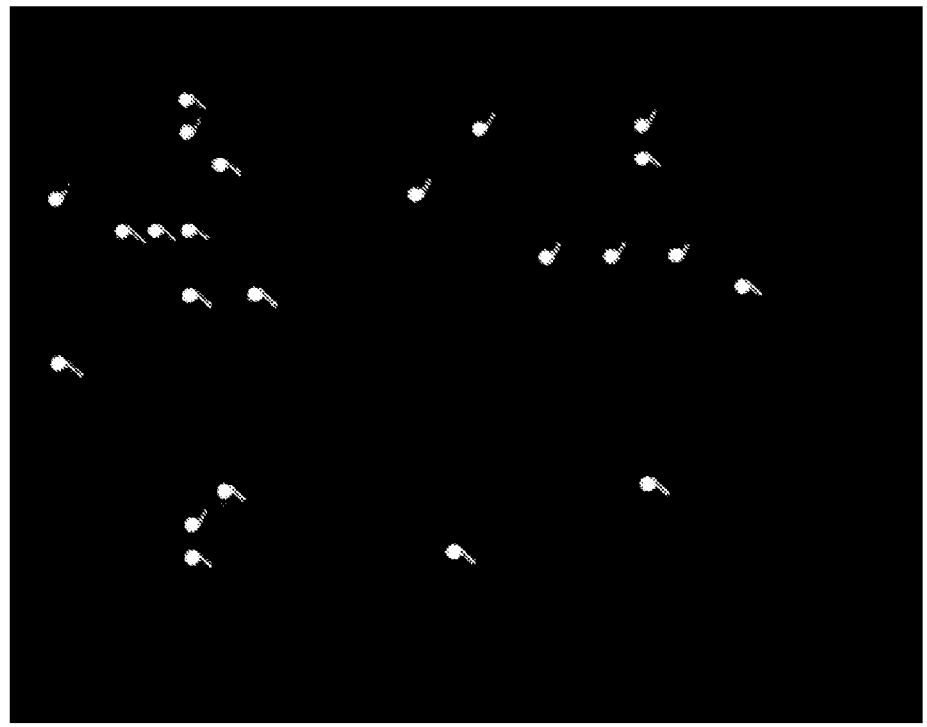
FIGS. 7-10 are photographs of assay results according to Example 1.
Figure 8:
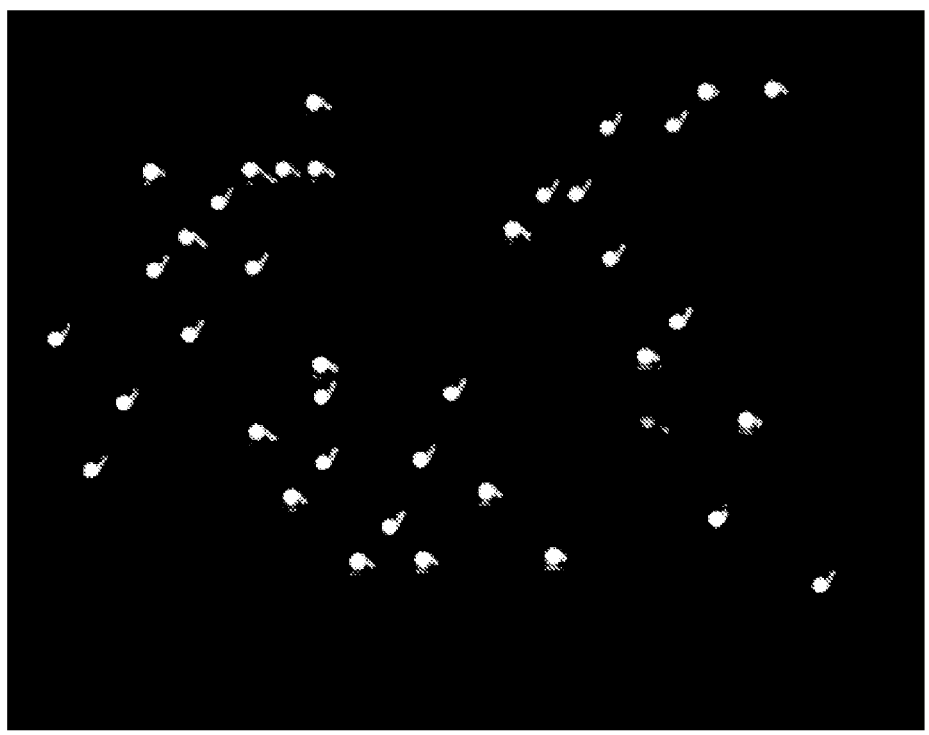
Figure 9:
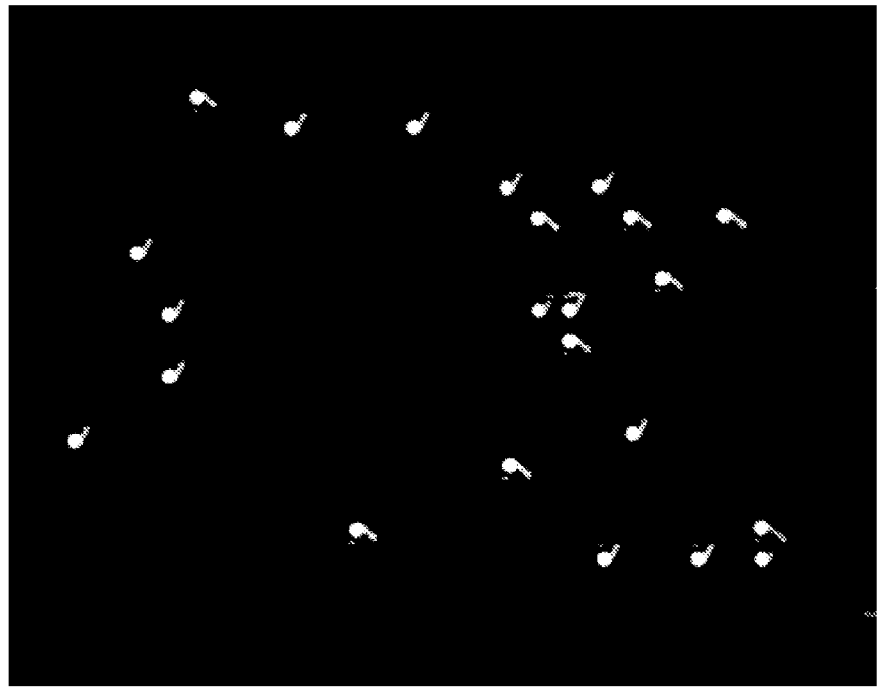
Figure 10:
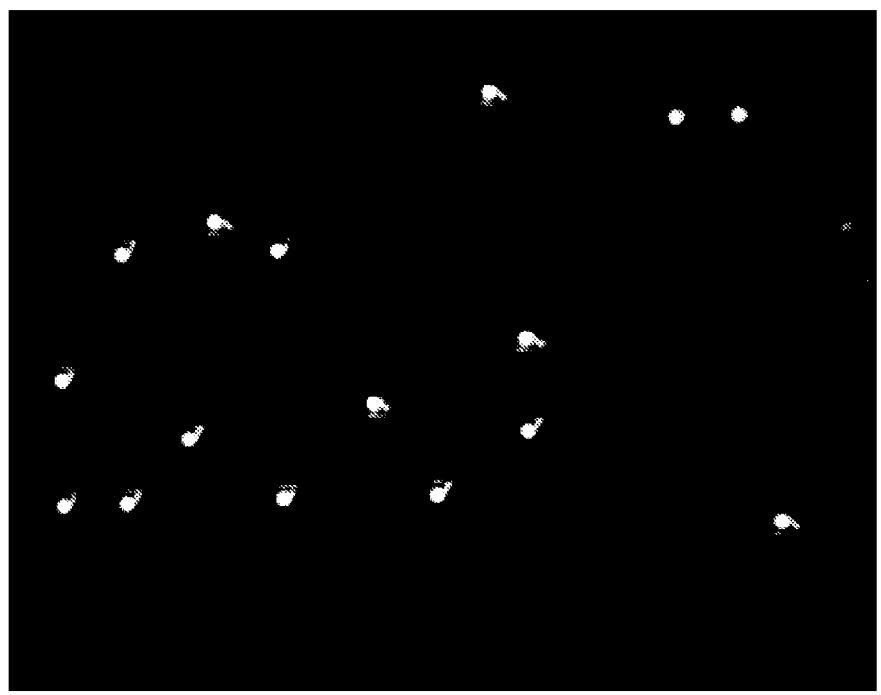

After incubation, each sample processing system was imaged on a gel reader (Alpha Innotech Chemimager model 5500, available from Alpha Innotech, San Leandro, Calif.) using overhead illumination (365 nm) and a UV cutoff filter. Images were acquired using 8-second exposure time. FIGS. 7-10 show the four images of the four replicate sample processing systems tested using the procedures outlined above, where FIG. 7 illustrates Replicate 1 of Table 1, FIG. 8 illustrates Replicate 2 of Table 1, FIG. 9 illustrates Replicate 3 of Table 1, and FIG. 10 illustrates Replicate 4 of Table 1. Additionally, the systems were placed in a fluorescence plate reader (available under the trade designation "SPECTRA-MAX," available from Molecular Devices, Sunnyvale, Calif.). The fluorescence intensity of each detection chamber 104 was determined using 350 nm excitation and 450 nm emission. In this manner, an "automated" readout was achieved.

Enumeration Using Most Probable Number

The formula MPN=N ln(N/N−X) was used to estimate the most probable number, where N is the total number of detection chambers and X is the number of "positive" compartments exhibiting fluorescence. Since the detection chambers did not contain a full milliliter of volume, the MPN value was multiplied by 1.74 (384 1.5-µL detection chambers). Table 1 shows the results from the four replicates that were tested using the procedure outlined above. In each device, 100 mL of sample was concentrated followed by 18 hours of incubation. A sample of the 100/mL dilution used to prepare the final 1/mL dilutions was also plated on 3M™ PETRIFILM™ EC plates (available from 3M Company, St. Paul, Minn.), indicating a count of 89 CFU/mL. Enumeration results calculated using the MPN formula for each replicate are shown in Table 1.

TABLE 1

ENUMERATION RESULTS FOR FOUR REPLICATES OF A SAMPLE PROCESSING SYSTEM

| REPLICATE | COUNT | MPN RESULT |
|---|---|---|
| 1 | 23 | 41 |
| 2 | 38 | 70 |
| 3 | 23 | 41 |
| 4 | 17 | 30 |

Example 2

Bacterial Enumeration Assay

Figure 11:
FIGS. 11-12 are photographs of assay results according to Example 2.
Figure 12:

Two replicates of a sample processing system were prepared according to the procedure outlined above in Example 1, except that the filters 120 were isoporous membranes (PORETICS® polycarbonate black membrane, 0.4 micron pore size, available from GE Osmonics, Minnetonka, Minn.). Filtration (i.e., concentration), elution, detection, and enumeration were performed as described above in Example 1. The ~100 cfu/mL sample used to prepare the final ~1/mL dilution was plated on a 3M™ PETRIFILM™ EC plate (available from 3M Company, St. Paul, Minn.), as a control. The images from two replicates are shown in FIGS. 11 and 12, where FIG. 11 illustrates Replicate 1 of Table 2, and FIG. 12 illustrates Replicate 2 of Table 2. Numerical results for the two replicates are shown in Table 2.

TABLE 2

ENUMERATION RESULTS FOR TWO REPLICATES OF A SAMPLE PROCESSING SYSTEM

| REPLICATE | COUNT | MPN RESULT | CONTROL COUNT |
|---|---|---|---|
| 1 | 23 | 40 | 24 |
| 2 | 9 | 16 | 21 |

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A method for processing samples, the method comprising:
    providing a loading chamber;
    providing a detection chamber positioned in fluid communication with the loading chamber;
    providing a fluid path defined at least partially by the loading chamber and the detection chamber, wherein the fluid path terminates at the detection chamber, such that the detection chamber includes an inlet but no outlet;
    positioning a sample in the loading chamber;
    filtering the sample with a filter positioned in the loading chamber to form a concentrated sample on the filter and a filtrate, the filter having an inlet and outlet and positioned such that at least one of the inlet and the outlet is positioned in the fluid path, wherein filtering includes applying a pressure differential across the filter;
    removing the filtrate from the fluid path at a location upstream of the detection chamber;
    moving at least a portion of the concentrated sample from the filter, in the fluid path, to the detection chamber by centrifugation; and
    analyzing the at least a portion of the concentrated sample in the detection chamber for an analyte of interest.

2. The method of claim 1, further comprising providing enrichment media in the detection chamber prior to moving at least a portion of the concentrated sample from the filter, in the fluid path, to the detection chamber.

3. The method of claim 1, wherein moving at least a portion of the concentrated sample from the filter, in the fluid path, to the detection chamber by centrifugation includes moving at least a portion of the concentrated sample to the detection chamber without exposing the concentrated sample to ambience.

4. The method of claim 1, wherein the inlet of the filter is positioned in the fluid path and the outlet is positioned such that removing the filtrate from the fluid path includes removing the filtrate via the outlet of the filter and occurs as a result of filtering the sample.

5. The method of claim 1, wherein the inlet and the outlet of the filter are positioned in the fluid path, such that the filtrate is removed from the fluid path at a location that is downstream of the filter.

6. The method of claim 1, wherein the fluid path is a primary fluid path and the filter defines a secondary fluid path, and wherein the secondary fluid path is oriented at an angle with respect to the primary fluid path.

7. The method of claim 1, further comprising eluting the concentrated sample from the filter in the fluid path.

8. The method of claim 1, wherein providing a detection chamber includes providing a plurality of detection chambers positioned in fluid communication with the loading chamber, wherein the fluid path terminates at each detection chamber, and wherein moving at least a portion of the concentrated sample from the filter, in the fluid path, to the detection chamber includes moving at least a portion of the concentrated sample in the fluid path to each of the plurality of detection chambers.

9. The method of claim 1, further comprising inhibiting the concentrated sample in the detection chamber from moving out of the detection chamber.

10. The method of claim 9, wherein inhibiting the concentrated sample in the detection chamber from moving out of the detection chamber includes positioning at least one of an obstruction and a seal in the fluid path upstream of the detection chamber.

11. The method of claim 1, wherein the detection chamber is in fluid communication with the loading chamber via a channel, wherein the fluid path is further defined by the channel, and further comprising sealing the channel after moving at least a portion of the concentrated sample in the fluid path to the detection chamber.

12. The method any claim 1, further comprising sealing at least a portion of the fluid path that is positioned upstream of the detection chamber after moving at least a portion of the concentrated sample from the filter, in the fluid path, to the detection chamber.

13. A system for processing samples, the system comprising:
   a loading chamber adapted to receive a sample;
   a detection chamber positioned in fluid communication with the loading chamber;
   a fluid path defined at least partially by the loading chamber and the detection chamber, wherein the fluid path terminates at the detection chamber, such that the detection chamber includes an inlet but no outlet;
   a filter positioned in the loading chamber and having an inlet and an outlet, the filter positioned such that at least one of the inlet and the outlet is positioned in the fluid path, the filter adapted to filter the sample to form a concentrated sample and a filtrate; and
   a filtrate outlet positioned such that the filtrate is removed from the fluid path at a location upstream of the detection chamber.

14. The system of claim 13, wherein the fluid path is configured to be sealed upstream of the detection chamber.

15. The system of claim 13, wherein the detection chamber is one of a plurality of detection chambers, wherein the fluid path terminates at each detection chamber, and wherein the fluid path is configured to be sealed upstream of each detection chamber.

16. The system of claim 13, wherein the detection chamber is one of a plurality of detection chambers positioned in fluid communication with the loading chamber, and wherein the loading chamber is one of a plurality of loading chambers, and wherein some of the plurality of detection chambers are positioned in fluid communication with each of the plurality of loading chambers.

17. The system of claim 13, further comprising enrichment media for an analyte of interest that is provided in the detection chamber.

18. The system of claim 17, wherein the enrichment media is present in the detection chamber prior to use.

19. The system of claim 13, further comprising a channel positioned in fluid communication between the loading chamber and the detection chamber, the channel further defining at least a portion of the fluid path.

20. The system of claim 19, wherein the detection chamber is one of a plurality of detection chambers positioned in fluid communication with the loading chamber, and wherein the channel is one of a plurality of channels positioned to fluidly couple the plurality of detection chambers with the loading chamber.

21. The system of claim 19, wherein the detection chamber is one of a plurality of detection chambers positioned in fluid communication with the loading chamber, and wherein the channel is a primary channel, and further comprising a plurality of secondary channels positioned to fluidly couple the plurality of detection chambers with the primary channel.

22. The system of claim 21, wherein the primary channel is configured to be sealed.

23. The system of claim 13, wherein the detection chamber is configured to receive at least a portion of the concentrated sample, and wherein, when at least a portion of the concentrate sample is positioned in the detection chamber, at least a portion of the fluid path upstream of the detection chamber is sealed.

* * * * *